US008389265B2

(12) United States Patent
Iida

(10) Patent No.: US 8,389,265 B2
(45) Date of Patent: Mar. 5, 2013

(54) GENE ASSOCIATED WITH FOAM FORMATION OF ACETIC ACID BACTERIUM, ACETIC ACID BACTERIUM BRED BY MODIFYING THE GENE AND METHOD FOR PRODUCING VINEGAR USING THE ACETIC ACID BACTERIUM

(75) Inventor: Aya Iida, Handa (JP)

(73) Assignee: Mizkan Group Corporation, Handa-Shi, Aichi (JP)

( * ) Notice: Subject to any disclaimer, the term of this patent is extended or adjusted under 35 U.S.C. 154(b) by 408 days.

(21) Appl. No.: 12/639,681

(22) Filed: Dec. 16, 2009

(65) Prior Publication Data

US 2010/0159541 A1 Jun. 24, 2010

(30) Foreign Application Priority Data

Dec. 24, 2008 (JP) ................. 2008-327795

(51) Int. Cl.
*C12N 1/20* (2006.01)
(52) U.S. Cl. .................................... 435/252.3
(58) Field of Classification Search ........................ None
See application file for complete search history.

(56) References Cited

FOREIGN PATENT DOCUMENTS

| JP | 2008-206413 | 9/2008 |
| JP | 2008-228660 | 10/2008 |
| WO | WO 01/14521 A1 | 3/2001 |

OTHER PUBLICATIONS

Iida et al, Identification and characterization of target genes of the GinI/GinR quorum-sensing system in Gluconacetobacter intermedius. Micrbiology. Sep. 2009;155(Pt 9):3021-32. Epub Jun. 11, 2009.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Guo et al, Protein tolerance to random amino acid change. Proc Natl Acad Sci U S A. Jun. 22, 2004;101(25):9205-9210. Epub Jun. 14, 2004.*
Fukushima, Jun, "Expression of Pathogenicity and quorum sensing system in *Pseudomonas aeruginosa*," Baiosaiensu to Indasutori (Bioscience and Industry) , vol. 60, No. 4, pp. 219-224 (2002).
Miyashita, Koichi; Sakamoto, Kazutoshi; Kitagaki, Hiroshi; Iwashita, Kazuhiro; Ito, Kiyoshi; Shimoi, Hitoshi, "Cloning and Analysis of the AWA1 Gene of a Nonfoaming Mutant of a Sake Yeast," Journal of Bioscience and Bioengineering, vol. 97, No. 1, pp. 14-18, (2004).
Certified English Translation of JP Patent Application No. JP 2008-327795 filed Dec. 24, 2008, 70 pages (including Declaration Statement of Accuracy).

* cited by examiner

*Primary Examiner* — Sheridan Swope
(74) *Attorney, Agent, or Firm* — Cadwalader, Wickersham & Taft LLP

(57) ABSTRACT

The present invention provides a method for reducing or deleting the function of a protein encoded by the glyT gene in an acetic acid-producing bacterium. This method significantly suppresses foam formation during the culture and enhances the acetic acid fermentation ability of the bacterium.

1 Claim, 6 Drawing Sheets

1. wild-type strain 2. glyT-disrupted strain 3. glyT complementary strain

Fig. 2
wild-type strain
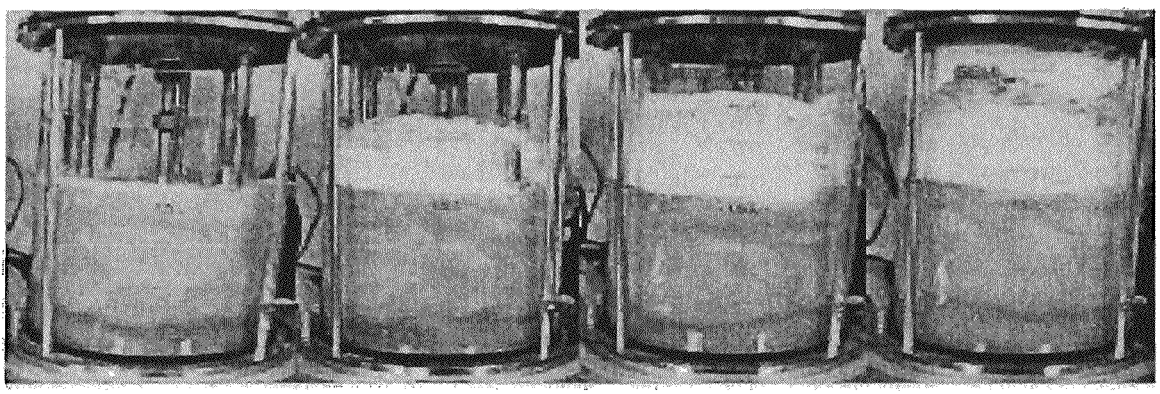
glyT-disrupted strain
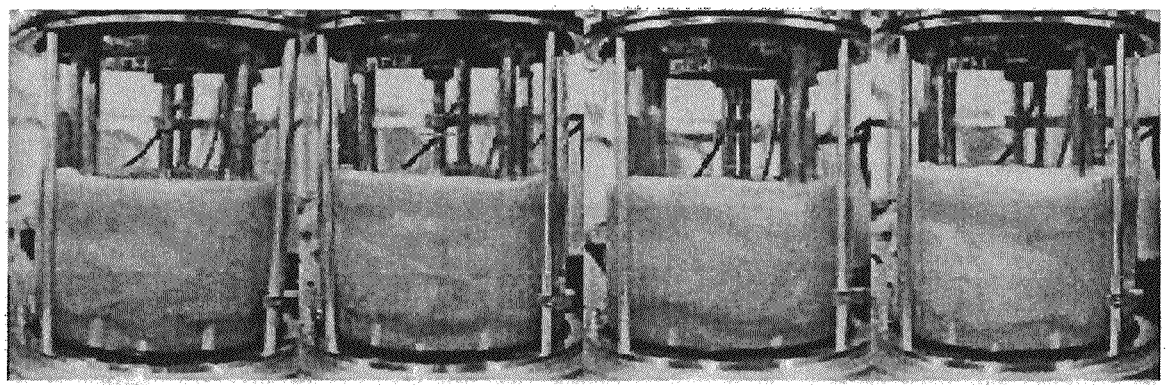
8     12     14     16 h

Fig. 4

| | | | | | | |
|---|---|---|---|---|---|---|
| CTGCAGGACC | CCAGGGCAAT | GCGGGTGCGC | GAACGGGTGC | GGCTGCATGG | CGCGATCATT | 60 |
| GCCTGTTTCG | CGCTGGGGGG | CGTGGGTGGC | GCGATCGGCT | ACCGGCTGTA | TGGCATGCGG | 120 |
| CTGCTGGTGC | TGCTGGGGGG | CGGGCTGGTC | ATGCTGGCCA | TACCGGGGCT | GTGGCGGGCA | 180 |
| AGGCATCCGC | GCTGAGGTCG | CCTGTCAGGC | ACTTGCATGG | CACCGGGTGC | TATTTTATCC | 240 |
| TTGGTGCATG | AAGCGCGGGC | ACGCCCGCGA | CCAGCGGGAG | CAGAACGTGA | TACAACAGAC | 300 |
| GAAAGCCACC | GAATTCCTGG | CCGCTCGCGG | CGTGCCCTTT | TCGGTGCATG | ATTATGAATA | 360 |
| CGCCCCCGGC | GGCGGCCTGA | TCGGGATGCA | GGCGGCGCAG | TCCATCGGGG | CAGACCCGGG | 420 |
| CTGTGTGCTC | AAGACGCTGG | TGGTGGAAGT | GGACCGCAGG | ACACCGGTCT | GCCTGGTGGT | 480 |
| GCCCGCCGAC | CACAAGGTAA | ATTTCAAGAA | GGTCGCGGCC | CTGTTCGATG | GCCGCAACGC | 540 |
| ACGGATGATG | AGCCCGGAAA | AATCAGCTGA | CCTGACCGGT | TTCCGCTCCG | GCGGGACCAG | 600 |
| CCCGTTCGGA | CAGGAGCATC | AGTTGCCCGT | CGTCCTGTCC | GCAGCCGCAA | TGGCGTGCCC | 660 |
| GCATGTCTAT | ATCAATGCTG | GCGACCAGGG | ACTGGTGGTG | CGCATTACCC | CCGCTGATGC | 720 |
| GCAGAAGGCG | GCAGATGCGC | AGGTGGGCCG | ATATTTCCGC | GCCGCCCGCC | CCGGCGGAAC | 780 |
| CAATCAAAAA | TTAACCTTTG | ACGTGCATAA | CCCGTCCCTG | AACAGAACAG | GGACAGGAAT | 840 |
| GCACGATGGC | TGTTTCCTCG | GATAATGCGG | AAATGGCTGC | CGGGTGGGCC | ACGTTCGATC | 900 |
| CCGCATGGTA | CTACGCCCGC | CATGCGGCGA | TGCTCGACCT | TATGGATATT | CCGCCCGAAC | 960 |
| AGGCGCAGGC | GTTTTATGAA | GCACACGGCG | CGGCGCTGGG | CCATTCGCCC | AATCCCTTTT | 1020 |
| TTGATGAGGA | CTGGTACCGC | GCCACCTATC | CCGATGTTGC | GCAGCAGGTG | CTGGCGGGCA | 1080 |
| CATGGCACAG | CGGGTCTGAC | CATTACCTGA | ATGCCGGGGCT | GGACACGCAC | GACCCGCACT | 1140 |
| GGCTGTTTGA | TACGCGCACC | TATCTGGCGG | CCTATCCCGA | CATCACGCCC | GCAACGCTGG | 1200 |
| CAGCCGGGGG | CTACCGCAAC | GCCTATGACC | ATTACCTGCG | CACGGGCGAT | GGGGAAATGC | 1260 |
| GCAGCGGGTC | GTGCTTTTTT | GATCCCGAAA | CCTACCTTGC | CCTGCTGGCG | GAATGCCAGC | 1320 |
| ACGACACCAT | TACGCACCCC | TTTGCCGATT | ACCTGCGCCG | GGGCATGGCC | GCCCTGCCCT | 1380 |
| GCCGCAGCGT | ATCGCTGTAT | TTCGATGCGG | AATGGTATGC | ACAGACCTAT | CCCGACGCCC | 1440 |
| ATGCGACACAT | TACGCAGGGC | ATGTGGCGCA | GAGCCCTACA | CCATTACCTG | TGCAATACCA | 1500 |
| CGCCGCAGGC | GTTCGATCCG | GGGCCATTCT | TTTCCGAATC | CTTCTATGCC | ATGGTCAACC | 1560 |
| CGGACGTGCT | CGGCGCGATC | GAGGCCGGAA | ACCTGCGCAA | CGGCTATGCC | CATTTCCTCA | 1620 |
| GTGATGGCGT | GCATGAACAG | CGCAAGCCGT | GTTCGACACT | GGACCTTGCG | CAGTACATGC | 1680 |
| GCGACCCTGG | CGTCCAGGCC | GATATCGCCG | CCCGCCGCGC | GCGCGACGGG | CTGGGCCATT | 1740 |
| ACCTTGCCGC | CCGCCCCGAC | CTGAAACCGC | CCCCACCGCC | GATGATCACG | GAAGAACAGG | 1800 |
| CCCGCACCCT | GTTCCGCCAC | ATGTGCAACG | CCCGCCTGCC | GCTGCTGCTG | AATGGCGGGA | 1860 |
| TCGATTTCAC | GTCTGATGCG | CCGCCTCGCGC | TGAGCGTCAT | CATCGTGGCG | CATGACCAGT | 1920 |
| TTGCGCTGAC | CATGTCCACG | CTTGCCTCGT | TACGCGCGAA | TTATCAGGGT | TCGATGCAGG | 1980 |
| TCCTGCTGGT | GGATTCCGGG | TCGCGCGATG | GCGTGGCCGG | GATCGAGGAC | CACGTGCCGG | 2040 |
| GGATCGAGGT | CCTGCGCTTT | GCGGGCAATA | TCGGGTTCGT | GCGCGGGTGC | AATGCGGCGC | 2100 |
| TGGCGCGGGT | GCGGGCACCT | GCCACGCTAT | ACCTCAACAA | CGACGTGGAC | CTGCAATATG | 2160 |
| GTGCGGTGGC | GCGCGCGCTG | TCGCGGCTTA | TGGCGGACGA | GGCGACCGGC | GCGGTCGGGG | 2220 |
| CCCGCGTCAT | CCGCACGCAT | GGCCTGCTGC | AGGAAGCGGG | CAGCCTGATC | TGGCGCGACG | 2280 |
| GATCTGTGCA | GGGCTACATG | CGCAGCCGCC | ATCGCGTGCT | GCCCGAAGCG | GGGTTCGTCC | 2340 |
| GCGCGGTGGA | TTTCTGTTCG | GGCGTGTTCC | TGATGGTCCG | GACGGACGTA | CTGCAGGTCG | 2400 |
| TTGACGGATT | CGATGAAAGC | TTCGCCCCCG | CCTATTTCGA | GGAAACCGAC | CTGTGCATGC | 2460 |
| GCATCCGCAC | GCTGGGATAC | CGGATCATGT | ACGACCCGGG | CGTCTGCCTT | GTGCATTATG | 2520 |
| AATGTGGCAC | GTCGGATGGA | ACCAGCGCGT | CACGACTGAT | CGCGCGCAAC | AACGACCTGT | 2580 |
| TCACCCGCAG | GCACGGTCCC | GCACTGCGGC | GCAGGCTGCT | GCGGCATGAT | CCCCTGCAGG | 2640 |
| CCCGCGCCCG | GCATGCGGAT | GACGGGCGCC | ACATCCTGTT | CATCGAGGAC | AGGCTGCCGC | 2700 |
| TGCGCCACCT | GGGATCGGGT | TTTACCCGGT | CGAATGACAT | CGTGACCACA | CTGGCGGGCC | 2780 |
| TTGGCTACCA | TGTTCCATCT | TTTCCCATCT | TCCCGCCCGAT | CGAAAGCGCC | GCGACACTCG | 2820 |
| CCGCCGCCTT | TCCCGAGACC | GTGGAGGTCA | TCCACGACCG | CGAACTGCCC | GATCTGCCCG | 2880 |
| ATTTCCTGCG | CGCGCGCAGC | GGGTGTTTCG | ACGCGATCTG | GATCGCCCGC | ACGCAGAACG | 2940 |
| CCGCCGGCGT | GGCCAGTATC | CTGAACGATG | CCGCATCCTG | CATTCCCGCC | GACCACATTG | 3000 |
| TGGTCGATAC | CGAGGCACTG | GTTGCCTGCC | GGGACATGGA | ATACGACCGC | TGCATGACCA | 3060 |
| TCACCCCGTC | ACCACCGCTG | TCCGAACGGC | TGGAACGTGA | ACTGCGCCCC | CTGTTCCTGG | 3120 |
| CGCAGCGCGT | GGTCGCGGTC | AACGCGGCGG | AGGCGGACCT | GCTGCGCGCC | GCGGGCTTTG | 3180 |
| ACAACGTGTC | GGTCCTTGGC | CACGTGCAGG | TCCCAAGCCG | CACCGGGCCG | GGATGGGCCA | 3240 |
| CACGGCGGGA | TATCCTGTTC | CTTGGCGCAGG | TTCATGAAAT | GCGCTCGCCG | AACCTCGACT | 3300 |
| CGCTCGCATG | GTTCAGTAGC | GAGGTCCTGC | CCCTGCTGGT | AGCGCAACTG | GGCGCGGATA | 3360 |
| TCCGGTTTAC | CGTCTGCGGC | CATACCGGAC | CGCGCGTTGA | CCTTGGCCCG | CTGCGCCACA | 3420 |
| ATCCCAACGT | GCGCATGCTG | GGCCGTGTCG | CGGACACTGC | CCCGGTTTAC | GACCAACACC | 3480 |
| GCGTGTTCGT | GGCACCGACC | CGCTATGCCC | CCGGTATTGC | CTACAAACTG | CATGAAGCCG | 3540 |
| CCGCCAACGG | CCTGCCGGTA | GTCGGGTGCC | CGCTATTGTG | CCAGCAGGCG | GGCTGGCGCG | 3600 |
| ACGGGCAGGA | CATGCTGTGC | GCCAGTGTTA | CGGACCCGGC | GGATTTTGCG | CGGCAGGTCG | 3660 |
| TGCGCCTCTA | TCATGACCAG | ACCCTGTGGG | ACACGTGGGA | GGACAACGCA | CTGACCCGCA | 3720 |
| TCGCCACCGA | ACATGCCCCG | CAGGATTACG | CCAGCCGGGT | GGCACATCC | ATGAACGCCG | 3780 |
| TATTCACACC | GGGATAAGGG | CCAGACCTGT | TTCCGGCACG | TTACCAACAG | GAACCGGAAA | 3840 |
| CATGACCCAG | ACGAAAATA | TTTCCTTTGC | CCCCGGCATT | GACGCAACCC | TGCACGACCG | 3900 |
| GGTGCTGGAC | GCACCGCATT | TCCGCCGGTG | GTATCAGGGC | ATGCGCGAAC | GCTTCACCCT | 3960 |
| GCGCCACGTG | CTGGTGCGCG | ACGCCATTGC | CTTTGATGCA | CACCGCATGG | GATTCATACT | 4020 |
| GGTCGAGGCC | GATGCCCTGC | ATGACGGTCA | CCGCGTTCCA | GGCATTGCAT | TGCTGCGCGG | 4080 |
| GGATTCCGTA | TCGGTGCTGC | TGGTGCTGAA | ATGCCCCGGC | TATCCCGACC | GGACCGTGGT | 4140 |
| C | | | | | | 4141 |

Fig. 5

| | | |
|---|---|---|
| MetAlaValSerSerAspAsnAlaGluMet | AlaAlaGlyTrpAlaThrPheAspProAla | 20 |
| TrpTyrTyrAlaArgHisAlaAlaMetLeu | AspLeuMetAspIleProProGluGlnAla | 40 |
| GlnAlaPheTyrGluAlaHisGlyAlaAla | LeuGlyHisSerProAsnProPhePheAsp | 60 |
| GluAspTrpTyrArgAlaThrTyrProAsp | ValAlaGlnGlnValLeuAlaGlyThrTrp | 80 |
| HisSerGlyPheAspHisTyrLeuAsnAla | GlyLeuAspThrHisAspProHisTrpLeu | 100 |
| PheAspThrArgThrTyrLeuAlaAlaTyr | ProAspIleThrProAlaThrLeuAlaAla | 120 |
| GlyGlyTyrArgAsnAlaTyrAspHisTyr | LeuArgThrGlyAspGlyGluMetArgSer | 140 |
| GlySerCysPhePheAspProGluThrTyr | LeuAlaLeuLeuAlaGluCysGlnHisAsp | 160 |
| ThrIleThrHisProPheAlaAspTyrLeu | ArgArgGlyMetAlaAlaLeuProCysArg | 180 |
| SerValSerLeuTyrPheAspAlaGluTrp | TyrAlaGlnThrTyrProAspAlaHisAla | 200 |
| AspIleThrGlnGlyMetTrpArgGlyAla | LeuHisHisTyrLeuCysAsnThrThrPro | 220 |
| GlnAlaPheAspProGlyProPhePheSer | GluSerPheTyrAlaMetValAsnProAsp | 240 |
| ValLeuGlyAlaIleGluAlaGlyAsnLeu | ArgAsnGlyTyrAlaHisPheLeuSerAsp | 260 |
| GlyValHisGluGlnArgLysProCysSer | ThrLeuAspLeuAlaGlnTyrMetArgAsp | 280 |
| ProGlyValGlnAlaAspIleAlaAlaArg | ArgAlaArgAspGlyLeuGlyHisTyrLeu | 300 |
| AlaAlaArgProAspLeuLysProProPro | ProProMetIleThrGluGlnAlaArg | 320 |
| ThrLeuPheArgHisMetCysAsnAlaArg | LeuProLeuLeuLeuAsnGlyIleIleAsp | 340 |
| PheThrSerAspAlaProProAlaLeuSer | ValIleIleValAlaHisAspGlnPheAla | 360 |
| LeuThrMetSerThrLeuAlaSerLeuArg | AlaAsnTyrHisGlySerMetGlnValLeu | 380 |
| LeuValAspSerGlySerArgAspGlyVal | AlaGlyIleGluAspHisValArgGlyIle | 400 |
| GluValLeuArgPheAlaGlyAsnIleGly | PheValArgGlyCysAsnAlaAlaLeuAla | 420 |
| ArgValArgAlaProAlaThrLeuTyrLeu | AsnAsnAspValAspLeuGlnTyrGlyAla | 440 |
| ValAlaArgAlaLeuSerArgLeuMetAla | AspGluAlaThrGlyAlaValGlyAlaArg | 460 |
| ValIleArgThrHisGlyLeuLeuGlnGlu | AlaGlySerLeuIleTrpArgAspGlySer | 480 |
| ValGlnGlyTyrMetArgAspAlaHisPro | CysValProGluAlaGlyPheValArgAla | 500 |
| ValAspPheCysSerGlyValPheLeuMet | ValArgThrAspValLeuGlnValLeuAsp | 520 |
| GlyPheAspGluSerPheAlaProAlaTyr | PheGluThrAspLeuCysMetArgIle | 540 |
| ArgThrLeuGlyTyrArgIleMetTyrAsp | ProGlyValCysLeuValHisTyrGluCys | 560 |
| GlyThrSerAspGlyThrSerAlaSerArg | LeuIleAlaArgAsnAsnAspLeuPheThr | 580 |
| ArgArgHisGlyProAlaLeuArgArgArg | LeuLeuArgHisAspProLeuGlnAlaArg | 600 |
| AlaArgHisAlaAspAspGlyArgHisIle | LeuPheIleGluAspArgLeuProLeuArg | 620 |
| HisLeuGlySerGlyPheThrArgSerAsn | AspIleValThrThrLeuAlaGlyLeuGly | 640 |
| TyrHisValThrValPheProIlePheArg | ProIleGluSerAlaAlaThrLeuAlaAla | 660 |
| AlaPheProGluThrValGluValIleHis | AspArgGluLeuProAspLeuProAspPhe | 680 |
| LeuArgAlaArgSerGlyCysPheAspAla | IleTrpIleAlaArgThrGlnAsnAlaAla | 700 |
| ArgValAlaSerIleLeuAsnAspAlaAla | SerCysIleProAlaAspHisIleValVal | 720 |
| AspThrGluAlaLeuValAlaCysArgAsp | MetGluTyrAspArgLeuHisAspIleThr | 740 |
| ProSerProProLeuSerGluArgLeuGlu | ArgGluLeuArgProLeuPheLeuAlaGln | 760 |
| ArgValValAlaValAsnAlaAlaGluAla | AspLeuLeuArgAlaAlaGlyPheAspAsn | 780 |
| ValSerValLeuGlyHisValGlnValPro | ArgProThrGlyProGlyTrpAlaAlaArg | 800 |
| ArgAspIleLeuPheLeuGlyAlaValHis | GluMetArgSerProAsnLeuAspSerLeu | 820 |
| AlaTrpPheSerSerGluValLeuProLeu | LeuValAlaGlnLeuGlyAlaAspIleArg | 840 |
| PheThrValCysGlyHisThrGlyProArg | ValAspLeuGlyProLeuArgHisAsnPro | 860 |
| AsnValArgMetLeuGlyArgValAlaAsp | ThrAlaProValTyrAspGlnHisArgVal | 880 |
| PheValAlaProThrArgTyrAlaAlaGly | IleAlaTyrLysLeuHisGluAlaAlaAla | 900 |
| AsnGlyLeuProValValGlySerProLeu | LeuCysGlnAlaGlyTrpArgAspGly | 920 |
| GlnAspMetLeuCysAlaSerValThrAsp | ProAlaAspPheAlaArgGlnValValArg | 940 |
| LeuTyrHisAspGlnThrLeuTrpAspThr | ValArgAspAsnAlaLeuThrArgIleAla | 960 |
| ThrGluHisAlaProGlnAspTyrAlaSer | ArgValAlaAspIleMetAsnAlaValPhe | 980 |
| ThrProGly | | 983 |

Fig. 6

5'-GGCAAGCTTGCAATTATCAGGCTGGCACC-3'

Fig. 7

5'-GCCAAGCTTACCAGGTGCGTGAGGGCATG-3'

Fig. 8

5'-CCGGGATCGAGGACCACGTG-3'

Fig. 9

5'-GCCTCTAGAACCCGGTCGTGCAGGGTTGC-3'

SEQUENCE LISTING

<160> NUMBER OF SEQ ID NOS: 6

<210> SEQ ID NO 1
<211> LENGTH: 4141
<212> TYPE: DNA
<213> ORGANISM: Gluconacetobacter intermedius

<400> SEQUENCE: 1

```
ctgcaggacc ccagggcaat gcgggtgcgc gaacgggtgc ggctgcatgg cgcgatcatt      60
gcctgtttcg cgctgggggg cgtgggtggc gcgatcggct accggctgta tggcatgcgg     120
ctgctggtgc tgctgggggg cgggctggtc atgctggcca taccggggct gtggcgggca     180
aggcatccgc gctgaggtcg cctgtcaggc acttgcatgg caccgggtgc tattttatcc     240
ttggtgcatg aagcgcgggc acgcccgcga ccagcggag cagaacgtga tacaacagac     300
gaaagccacc gaattcctgg ccgctcgcgg cgtgcccttt tcggtgcatg attatgaata     360
cgcccccggc ggcggcctga tcgggatgca ggcggcgcag tccatcgggg cagacccggg     420
ctgtgtgctc aagacgctgg tggtggaagt ggaccgcagg acaccggtct gcctggtggt     480
gcccgccgac cacaaggtaa atttcaagaa ggtcgcggcc ctgttcgatg gccgcaacgc     540
acggatgatg agcccggaaa aatcagctga cctgaccggt ttccgctccg gcgggaccag     600
cccgttcgga caggagcatc agttgcccgt cgtcctgtcc gcagccgcaa tggcgtgccc     660
gcatgtctat atcaatgctg gcgaccaggg actggtggtg cgcattaccc ccgctgatgc     720
gcagaaggcg gcagatgcgc aggtgggccg atatttccgc gccgcccgcc ccggcggaac     780
caatcaaaaa ttaacctttg acgtgcataa cccgtccctg aacagaacag ggacaggaat     840
gcacgatggc tgtttcctcg gataatgcgg aaatggctgc cgggtgggcc acgttcgatc     900
ccgcatggta ctacgcccgc catgcggcga tgctcgacct tatggatatt ccgcccgaac     960
aggcgcaggc gttttatgaa gcacacggcg cggcgctggg ccattcgccc aatcccttt     1020
ttgatgagga ctggtaccgc gccacctatc ccgatgttgc gcagcaggtg ctggcgggca    1080
catggcacag cggttcgac cattacctga atgcggggct ggacacgcac gaccgcact     1140
ggctgtttga tacgcgcacc tatctggcgg cctatcccga catcacgccc gcaacgctgg    1200
cagccggggg ctaccgcaac gcctatgacc attacctgcg cacgggcgat ggggaaatgc    1260
gcagcgggtc gtgctttttt gatcccgaaa cctaccttgc cctgctggcg gaatgccagc    1320
acgacaccat tacgcacccc tttgccgatt acctgcgccg gggcatggcc gccctgccct    1380
gccgcagcgt atcgctgtat ttcgatgcgg aatggtatgc acagacctat cccgacgccc    1440
atgcggacat tacgcagggc atgtggcgcg gagccctgca ccattacctg tgcaatacca    1500
cgccgcaggc gttcgatccg gggccattct tttccgaatc cttctatgcc atggtcaacc    1560
cggacgtgct cggcgcgatc gaggccggaa acctgcgcaa cggctatgcc catttcctca    1620
gtgatggcgt gcatgaacag cgcaagccgt gttcgacact ggaccttgcg cagtacatgc    1680
gcgaccctgg cgtccaggcc gatatcgccc ccgccgcgc gcgcgacggg ctgggccatt    1740
accttgccgc ccgccccgac ctgaaaccgc ccccaccgcc gatgatcacg gaagaacagg    1800
cccgcaccct gttccgccac atgtgcaacg cccgcctgcc gctgctgctg aatggcggga    1860
```

```
tcgatttcac gtctgatgcg ccgcctgcgc tgagcgtcat catcgtggcg catgaccagt   1920
ttgcgctgac catgtccacc cttgcctcgt tacgcgcgaa ttatcacggg tcgatgcagg   1980
tcctgctggt ggattccggg tcgcgcgatg gcgtggccgg gatcgaggac cacgtgcgcg   2040
ggatcgaggt cctgcgcttt gcgggcaata tcggttcgt gcgcgggtgc aatgcggcgc   2100
tggcgcgggt gcgggcacct gccacgctat acctcaacaa cgacgtggac ctgcaatatg   2160
gtgcggtggc gcgcgcgctg tcgcggctta tggcggacga ggcgaccggc gcggtcgggg   2220
cccgcgtcat ccgcacgcat ggcctgctgc aggaagcggg cagcctgatc tggcgcgacg   2280
gatctgtgca gggctacatg cgcgacgccc atccgtgcgt gcccgaagcg gggttcgtcc   2340
gcgcggtgga tttctgttcg ggcgtgttcc tgatggtccg gacggacgta ctgcaggtgc   2400
ttgacggatt cgatgaaagc ttcgcccccg cctatttcga ggaaaccgac ctgtgcatgc   2460
gcatccgcac gctgggatac cggatcatgt acgacccggg cgtctgcctt gtgcattatg   2520
aatgtggcac gtcggatgga accagcgcgt cacgactgat cgcgcgcaac aacgacctgt   2580
tcacccgcag gcacggtccc gcactgcggc gcaggctgct gcggcatgat cccctgcagg   2640
cccgcgcccg gcatgcggat gacgggcgcc acatcctgtt catcgaggac aggctgccgc   2700
tgcgccacct gggatcgggt tttacccggt cgaatgacat cgtgaccaca ctggcgggcc   2760
ttggctacca tgttacggtc tttcccatct tccgcccgat cgaaagcgcc gcgacactgg   2820
ccgccgcctt tcccgagacc gtggaggtca tccacgaccg cgaactgccc gatctgcccg   2880
atttcctgcg cgcgcgcagc gggtgtttcg acgcgatctg gatcgcccgc acgcagaacg   2940
ccgcccgcgt ggccagtatc ctgaacgatg ccgcatcctg cattcccgcc gaccacattg   3000
tggtcgatac cgaggcactg gttgcctgcc gggacatgga atacgaccgc ctgcatgaca   3060 tcacccgtc accaccgctg tccgaacggc tggaacgtga actgcgcccc ctgttcctgg   3120
cgcagcgcgt ggtcgcggtc aacgcggcgg aggcggacct gctgcgcgcc gcgggctttg   3180
acaacgtgtc ggtccttggc cacgtgcagg tcccaaggcc caccgggccg ggatgggccg   3240
cacggcggga tatcctgttc cttggcgcgg ttcatgaaat gcgctcgccc aacctcgact   3300
cgctcgcatg gttcagtagc gaggtcctgc ccctgctggt agcgcaactg ggcgcggata   3360
tccggtttac cgtctgcggc cataccggac cgcgcgttga ccttggcccg ctgcgccaca   3420
atcccaacgt gcgcatgctg ggccgtgtcg cggacactgc cccggtttac gaccaacacc   3480
gcgtgttcgt ggcaccgacc cgctatgccg ccggtattgc ctacaaactg catgaagccg   3540
ccgccaacgg cctgccggta gtcgggtcgc cgctattgtg ccagcaggcg ggctggcgcg   3600
acgggcagga catgctgtgc gccagtgtta cggacccggc ggattttgcg cggcaggtcg   3660
tgcgcctcta tcatgaccag accctgtggg acacggtgcg ggacaacgca ctgacccgca   3720
tcgccaccga acatgccccg caggattacg ccagccgggt ggcggacatc atgaacgccg   3780
tattcacacc gggataaggg ccagacctgt ttccggcacg ttaccaacag gaaccggaaa   3840
catgacccag acggaaaata tttcctttgc ccccggcatt gacgcaaccc tgcacgaccg   3900
ggtgctggac gcaccgcatt ccgccggtg gtatcagggc atgcgcgaac gcttcaccct   3960
gcgccacgtg ctggtgcgcg acgccattgc ctttgatgca caccgcatgg gattcatact   4020
ggtcgaggcc gatgccctgc atgacggtca ccgcgttcca ggcattgcat tgctgcgcgg   4080
ggattccgta tcggtgctgc tggtgctgaa atgccccggc tatcccgacc ggaccgtggt   4140
c                                                                   4141
```

<210> SEQ ID NO 2
<211> LENGTH: 983
<212> TYPE: PRT
<213> ORGANISM: Gluconacetobacter intermedius

<400> SEQUENCE: 2

Met Ala Val Ser Ser Asp Asn Ala Glu Met Ala Gly Trp Ala Thr
1               5                   10                  15

Phe Asp Pro Ala Trp Tyr Tyr Ala Arg His Ala Met Leu Asp Leu
            20                  25                  30

Met Asp Ile Pro Pro Glu Gln Ala Gln Ala Phe Tyr Glu Ala His Gly
        35                  40                  45

Ala Ala Leu Gly His Ser Pro Asn Pro Phe Phe Asp Glu Asp Trp Tyr
    50                  55                  60

Arg Ala Thr Tyr Pro Asp Val Ala Gln Gln Val Leu Ala Gly Thr Trp
65                  70                  75                  80

His Ser Gly Phe Asp His Tyr Leu Asn Ala Gly Leu Asp Thr His Asp
                85                  90                  95

Pro His Trp Leu Phe Asp Thr Arg Thr Tyr Leu Ala Ala Tyr Pro Asp
            100                 105                 110

Ile Thr Pro Ala Thr Leu Ala Ala Gly Gly Tyr Arg Asn Ala Tyr Asp
        115                 120                 125

His Tyr Leu Arg Thr Gly Asp Gly Glu Met Arg Ser Gly Ser Cys Phe
    130                 135                 140

Phe Asp Pro Glu Thr Tyr Leu Ala Leu Leu Ala Glu Cys Gln His Asp
145                 150                 155                 160

Thr Ile Thr His Pro Phe Ala Asp Tyr Leu Arg Arg Gly Met Ala Ala
                165                 170                 175

Leu Pro Cys Arg Ser Val Ser Leu Tyr Phe Asp Ala Glu Trp Tyr Ala
            180                 185                 190

Gln Thr Tyr Pro Asp Ala His Ala Asp Ile Thr Gln Gly Met Trp Arg
        195                 200                 205

Gly Ala Leu His His Tyr Leu Cys Asn Thr Thr Pro Gln Ala Phe Asp
    210                 215                 220

Pro Gly Pro Phe Phe Ser Glu Ser Phe Tyr Ala Met Val Asn Pro Asp
225                 230                 235                 240

Val Leu Gly Ala Ile Glu Ala Gly Asn Leu Arg Asn Gly Tyr Ala His
                245                 250                 255

Phe Leu Ser Asp Gly Val His Glu Gln Arg Lys Pro Cys Ser Thr Leu
            260                 265                 270

Asp Leu Ala Gln Tyr Met Arg Asp Pro Gly Val Gln Ala Asp Ile Ala
        275                 280                 285

Ala Arg Arg Ala Arg Asp Gly Leu Gly His Tyr Leu Ala Ala Arg Pro
    290                 295                 300

Asp Leu Lys Pro Pro Pro Pro Met Ile Thr Glu Glu Gln Ala Arg
305                 310                 315                 320

Thr Leu Phe Arg His Met Cys Asn Ala Arg Leu Pro Leu Leu Leu Asn
                325                 330                 335

Gly Gly Ile Asp Phe Thr Ser Ala Pro Pro Ala Leu Ser Val Ile
            340                 345                 350

Ile Val Ala His Asp Gln Phe Ala Leu Thr Met Ser Thr Leu Ala Ser
        355                 360                 365

Leu Arg Ala Asn Tyr His Gly Ser Met Gln Val Leu Leu Val Asp Ser
    370                 375                 380

```
Gly Ser Arg Asp Gly Val Ala Gly Ile Glu Asp His Val Arg Gly Ile
385                 390                 395                 400

Glu Val Leu Arg Phe Ala Gly Asn Ile Gly Phe Val Arg Gly Cys Asn
            405                 410                 415

Ala Ala Leu Ala Arg Val Arg Ala Pro Ala Thr Leu Tyr Leu Asn Asn
        420                 425                 430

Asp Val Asp Leu Gln Tyr Gly Ala Val Ala Arg Ala Leu Ser Arg Leu
    435                 440                 445

Met Ala Asp Glu Ala Thr Gly Ala Val Gly Ala Arg Val Ile Arg Thr
450                 455                 460

His Gly Leu Leu Gln Glu Ala Gly Ser Leu Ile Trp Arg Asp Gly Ser
465                 470                 475                 480

Val Gln Gly Tyr Met Arg Asp Ala His Pro Cys Val Pro Glu Ala Gly
                485                 490                 495

Phe Val Arg Ala Val Asp Phe Cys Ser Gly Val Phe Leu Met Val Arg
            500                 505                 510

Thr Asp Val Leu Gln Val Leu Asp Gly Phe Asp Glu Ser Phe Ala Pro
        515                 520                 525

Ala Tyr Phe Glu Glu Thr Asp Leu Cys Met Arg Ile Arg Thr Leu Gly
530                 535                 540

Tyr Arg Ile Met Tyr Asp Pro Gly Val Cys Leu Val His Tyr Glu Cys
545                 550                 555                 560

Gly Thr Ser Asp Gly Thr Ser Ala Ser Arg Leu Ile Ala Arg Asn Asn
                565                 570                 575

Asp Leu Phe Thr Arg Arg His Gly Pro Ala Leu Arg Arg Leu Leu
            580                 585                 590

Arg His Asp Pro Leu Gln Ala Arg Ala Arg His Ala Asp Asp Gly Arg
        595                 600                 605

His Ile Leu Phe Ile Glu Asp Arg Leu Pro Leu Arg His Leu Gly Ser
    610                 615                 620

Gly Phe Thr Arg Ser Asn Asp Ile Val Thr Thr Leu Ala Gly Leu Gly
625                 630                 635                 640

Tyr His Val Thr Val Phe Pro Ile Phe Arg Pro Ile Glu Ser Ala Ala
                645                 650                 655

Thr Leu Ala Ala Ala Phe Pro Glu Thr Val Glu Val Ile His Asp Arg
            660                 665                 670

Glu Leu Pro Asp Leu Pro Asp Phe Leu Arg Ala Arg Ser Gly Cys Phe
        675                 680                 685

Asp Ala Ile Trp Ile Ala Arg Thr Gln Asn Ala Ala Arg Val Ala Ser
    690                 695                 700

Ile Leu Asn Asp Ala Ala Ser Cys Ile Pro Ala Asp His Ile Val Val
705                 710                 715                 720

Asp Thr Glu Ala Leu Val Ala Cys Arg Asp Met Glu Tyr Asp Arg Leu
                725                 730                 735

His Asp Ile Thr Pro Ser Pro Leu Ser Glu Arg Leu Glu Arg Glu
            740                 745                 750

Leu Arg Pro Leu Phe Leu Ala Gln Arg Val Val Ala Val Asn Ala Ala
        755                 760                 765

Glu Ala Asp Leu Leu Arg Ala Ala Gly Phe Asp Asn Val Ser Val Leu
    770                 775                 780

Gly His Val Gln Val Pro Arg Pro Thr Gly Pro Gly Trp Ala Ala Arg
785                 790                 795                 800

Arg Asp Ile Leu Phe Leu Gly Ala Val His Glu Met Arg Ser Pro Asn
                805                 810                 815
```

-continued

```
Leu Asp Ser Leu Ala Trp Phe Ser Ser Glu Val Pro Leu Leu Val
            820                 825                 830
Ala Gln Leu Gly Ala Asp Ile Arg Phe Thr Val Cys Gly His Thr Gly
        835                 840                 845
Pro Arg Val Asp Leu Gly Pro Leu Arg His Asn Pro Asn Val Arg Met
    850                 855                 860
Leu Gly Arg Val Ala Asp Thr Ala Pro Val Tyr Asp Gln His Arg Val
865                 870                 875                 880
Phe Val Ala Pro Thr Arg Tyr Ala Ala Gly Ile Ala Tyr Lys Leu His
                885                 890                 895
Glu Ala Ala Ala Asn Gly Leu Pro Val Val Gly Ser Pro Leu Leu Cys
            900                 905                 910
Gln Gln Ala Gly Trp Arg Asp Gly Gln Asp Met Leu Cys Ala Ser Val
        915                 920                 925
Thr Asp Pro Ala Asp Phe Ala Arg Gln Val Val Arg Leu Tyr His Asp
    930                 935                 940
Gln Thr Leu Trp Asp Thr Val Arg Asp Asn Ala Leu Thr Arg Ile Ala
945                 950                 955                 960
Thr Glu His Ala Pro Gln Asp Tyr Ala Ser Arg Val Ala Asp Ile Met
                965                 970                 975
Asn Ala Val Phe Thr Pro Gly
            980

<210> SEQ ID NO 3
<211> LENGTH: 29
<212> TYPE: DNA
<213> ORGANISM: Artificial
<220> FEATURE:
<223> OTHER INFORMATION: primer 1

<400> SEQUENCE: 3
ggcaagcttg caattatcag gctggcacc                              29

<210> SEQ ID NO 4
<211> LENGTH: 29
<212> TYPE: DNA
<213> ORGANISM: Artificial
<220> FEATURE:
<223> OTHER INFORMATION: primer 2

<400> SEQUENCE: 4
gccaagctta ccaggtgcgt gagggcatg                              29

<210> SEQ ID NO 5
<211> LENGTH: 20
<212> TYPE: DNA
<213> ORGANISM: Artificial
<220> FEATURE:
<223> OTHER INFORMATION: primer 3

<400> SEQUENCE: 5
ccgggatcga ggaccacgtg                                        20

<210> SEQ ID NO 6
<211> LENGTH: 29
<212> TYPE: DNA
<213> ORGANISM: Artificial
<220> FEATURE:
<223> OTHER INFORMATION: primer 4
```

```
<400> SEQUENCE: 6
gcctctagaa cccggtcgtg cagggttgc                                           29
```

GENE ASSOCIATED WITH FOAM FORMATION OF ACETIC ACID BACTERIUM, ACETIC ACID BACTERIUM BRED BY MODIFYING THE GENE AND METHOD FOR PRODUCING VINEGAR USING THE ACETIC ACID BACTERIUM

CROSS-REFERENCE TO RELATED APPLICATIONS

This application claims benefit of Japan Patent Application No. JP2008-327795, filed Dec. 24, 2008, the disclosure of which is incorporated, in its entirety, by this reference.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION (1) Field of the Invention

The present invention relates to a gene involved in foam formation during microorganism culture. The present invention further relates to an acetic acid bacterium which is bred by reducing or deleting the function of a protein encoded by the gene involved in foam formation and which thus has a suppressed foaming ability during culture and generates a larger amount of acetic acid. The present invention still further relates to a method for producing vinegar using the acetic acid bacterium, and vinegar produced by the production method.

(2) Description of Related Art

Foam formation during microorganism culture is a major concern in the food industry and chemical industry where microorganisms are utilized. In many cases, foam is generated when microorganisms are cultured, especially when cultured under aeration and agitation. A foam layer is formed at the upper part of the culture tank and raises problems such as reduction of the working volume in the culture tank, or loss of the culture broth, compositional change of the broth and leakage of the microorganisms due to the outflow of the foam from the upper part of the tank. As such, foam formation causes problems including decrease in the production efficiency and deterioration in quality as well as environmental problems. For this reason, it has been a critical object to suppress foam formation when obtaining products by an efficient culture of microorganisms. Decrease in the production efficiency due to foam formation has similarly been a problem in vinegar production using an acetic acid bacterium.

Therefore, physical and chemical methods have been developed as defoaming methods. Physical methods include a mechanical method in which a shear force is applied to foam by such means as an agitating blade to destroy the foam, thermal method in which a liquid viscosity is decreased by heating to destabilize the foam, and electric method in which foam is broken by means such as energization, sparking and electric current. All of these methods, however, raise cost by introducing and using equipment. In addition, defoaming results brought by these methods have been insufficient.

Chemical methods include adding antifoaming agents. Compounds such as alcohols, esters, fatty acids and silicon are used as antifoaming agents. However, while a defoaming method using an antifoaming agent is simple, there have been problems caused by some antifoaming agents such as decrease in the oxygen transfer rate which is important for microorganism growth and the material production, inhibition of the microorganism growth, and adverse influence on the isolation and purification steps.

Although the foam formation mechanism during microorganism culture remains largely unknown, some genes and proteins involved in foam formation in eukaryotes have been found. One of those genes is the awa1 gene, which is involved in foam formation and found in yeast (see for example, Non-patent document 1). This gene encodes the glycosylphosphatidylinositol anchor protein which is a protein specific to eukaryotes and this protein is involved in the cell surface hydrophobicity, and foam formation is suppressed when the gene encoding this protein is disrupted.

Further, a protein called Hydrophobin which is either hydrophobic or amphipathic was found in fungi, mushrooms, etc., and it has been found that foam formation is suppressed by disrupting the gene encoding Hydrophobin (see for example, Patent document 1).

In prokaryotes, however, knowledge of genes or proteins involved in foam formation during culture is scarcely obtained. For prokaryotes, therefore, breeding of bacterial strains with less foam formation has been desired as a novel defoaming means to replace the physical or chemical methods.

The presence of an intercellular signal communication system in which transcription of specific genes is controlled depending on the cell density has been recently elucidated in many bacteria. This system is called quorum-sensing system (a control system sensing cell density) and is involved in the expression control for various functions such as bioluminescence, exoenzyme production, virulence expression, biofilm formation, and antibiotic production.

For example, two kinds of proteins are involved in the quorum-sensing system which has been found in many Gram negative bacteria such as *Vibrio fischeri* (see for example, Non-Patent document 2: Fukushima, Jun, "Expression of pathogenicity and quorum sensing system in *Pseudomonas aeruginosa*," Bioscience and Industry, Vol. 60, No. 4, pp. 219-224 (2002)). One is an Acyl Homoserine Lactone Synthase, that synthesizes acyl homoserine lactone which is an intracellular signal molecule, and the other is an Acyl Homoserine Lactone Receptor-Type Transcription Factor, that is a receptor of acyl homoserine lactone and that also functions as a transcription factor.

Acyl homoserine lactone produced by Acyl Homoserine Lactone Synthase in a bacterial cell diffuses inside and outside the bacterial cell. As the concentration of acyl homoserine lactone is increased, it forms a complex with the Acyl Homoserine Lactone Receptor-Type Transcription Factor in the bacterial cell to control the gene transcription.

The present inventor has already obtained two kinds of genes involved in the quorum-sensing system in an acetic acid bacterium, namely, a gene encoding the Acyl Homoserine Lactone Synthase (hereinafter may be referred to as orf1) and a gene encoding the Acyl Homoserine Lactone Receptor-Type Transcription Factor (hereinafter may be referred to as orf2) and has demonstrated that the quorum-sensing system in an acetic acid bacterium is involved in the acetic acid production ability (see for example, Patent document 2).

Further, despite that the nexus between the quorum-sensing system and foam formation during microorganism culture had been totally unknown, the present inventor obtained a gene involved in foam formation during culture of an acetic acid bacterium (hereinafter may be referred to as orf3) as a gene involved in the quorum-sensing system of an acetic acid bacterium, modified the gene, and demonstrated that reducing or deleting the function of a protein encoded by the gene can suppress foam formation during culture of an acetic acid bacterium and increase the ability of an acetic acid bacterium to produce acetic acid (see for example, Patent document 3).

However, the whole picture of a family of genes involved in the quorum-sensing system of an acetic acid bacterium has not yet been sufficiently elucidated and it is possible that there are genes involved in foam formation during culture of an acetic acid bacterium other than the above genes. It has thus been expected that the gene can strongly improve the acetic acid production ability.

Non-Patent Document 1: Journal of bioscience and bioengineering, Vol. 97, No. 1, pp. 14-18, 2004.
Non-Patent Document 2: Bioscience and Industry, Vol. 60, No. 4, pp. 219-224, 2002.
Patent Document 1: Published Japanese translation of PCT international publication No. 2003-507056.
Patent Document 2: Japanese Laid-Open Patent Application No. 2008-206413.
Patent Document 3: Japanese Laid-Open Patent Application No. 2008-228660.

BRIEF SUMMARY OF THE INVENTION

The objects of the present invention are (1) to provide a method for suppressing foaming ability of an acetic acid bacterium during culture by obtaining a novel gene involved in foam formation and accordingly reducing or deleting the function of the protein encoded by the gene, (2) to provide a method for more efficiently producing vinegar containing a high concentration of acetic acid by using the acetic acid bacterium with suppressed foaming ability bred by the method, and (3) to provide vinegar produced by said production method.

The present inventor conducted a comprehensive microarray analysis on gene expression for the wild-type strain and a disrupted strain of the orf1 gene encoding the Acyl Homoserine Lactone Synthase, which is one of the components of the quorum-sensing system (hereinafter may be referred to as orf1-disrupted strain). Consequently, the present inventor found a novel gene glyT, the transcript amount of which is decreased in the orf1-disrupted strain as compared to the wild-type strain, meaning that this novel gene glyT is thought to be under the control of the quorum-sensing system.

The present inventor then modified glyT, obtained an acetic acid bacterium with significantly suppressed foam formation and significantly enhanced acetic acid fermentation ability by reducing or deleting the function of a protein encoded by glyT, and found that vinegar containing a high concentration of acetic acid can be more efficiently produced with the use of this acetic acid bacterium. The present invention was thus completed.

The present invention relates to the following.
(1) A protein shown by following (A), (B) or (C):
(A) a protein consisting of the amino acid sequence shown by SEQ ID NO: 2 in the sequence listing;
(B) a protein which consists of an amino acid sequence wherein one or a few amino acids are substituted, deleted, inserted or added in the amino acid sequence shown by SEQ ID NO: 2 in the sequence listing, and which is involved in foam formation during culture of an acetic acid bacterium;
(C) a protein which consists of an amino acid sequence having at least 85% or more identity to the amino acid sequence shown by SEQ ID NO: 2 in the sequence listing, and which is involved in foam formation during culture of an acetic acid bacterium.
(2) A DNA encoding a protein shown by following (A), (B) or (C):
(A) a protein consisting of the amino acid sequence shown by SEQ ID NO: 2 in the sequence listing;
(B) a protein which consists of an amino acid sequence wherein one or a few amino acids are substituted, deleted, inserted or added in the amino acid sequence shown by SEQ ID NO: 2 in the sequence listing, and which is involved in foam formation during culture of an acetic acid bacterium;
(C) a protein which consists of an amino acid sequence having at least 85% or more identity to the amino acid sequence shown by SEQ ID NO: 2 in the sequence listing, and which is involved in foam formation during culture of an acetic acid bacterium.
(3) A DNA shown by following (A), (B), (C) or (D):
(A) a DNA consisting of the nucleotide sequence of nucleotide numbers 846 to 3794 in the nucleotide sequence shown by SEQ ID NO: 1 in the sequence listing;
(B) a DNA which hybridizes under stringent conditions to a DNA consisting of a sequence complementary to the nucleotide sequence of nucleotide numbers 846 to 3794 in the nucleotide sequence shown by SEQ ID NO: 1 in the sequence listing, and which encodes a protein involved in foam formation during culture of an acetic acid bacterium;
(C) a DNA which hybridizes under stringent conditions to a DNA consisting of a nucleotide sequence produced from a part of the nucleotide sequence of nucleotide numbers 846 to 3794 in the nucleotide sequence shown by SEQ ID NO: 1 in the sequence listing and having the function as a primer or a probe, and which encodes a protein involved in foam formation during culture of an acetic acid bacterium;
(D) a DNA which consists of a nucleotide sequence wherein one or a few nucleotides are substituted, deleted, inserted or added in the nucleotide sequence of nucleotide numbers 846 to 3794 in the nucleotide sequence shown by SEQ ID NO: 1 in the sequence listing, and which encodes a protein involved in foam formation during culture of an acetic acid bacterium.
(4) A method for producing an acetic acid bacterium with suppressed foaming ability, wherein the function of a protein which is encoded by the DNA according to (2) or (3) is reduced or deleted.
(5) An acetic acid bacterium with suppressed foaming ability which is obtained by the method according to (4).
(6) The acetic acid bacterium with suppressed foaming ability according to (5), wherein the acetic acid bacterium is *Gluconacetobacter intermedius* NCI1051ΔglyT (FERM BP-11068).
(7) A method for producing vinegar comprising culturing the acetic acid bacterium according to (5) or (6) in an alcohol-containing medium, and generating and accumulating acetic acid in the medium.

According to the present invention, a gene involved in foam formation during culture of an acetic acid bacterium and a protein encoded by the gene are provided. Further provided is a method for significantly suppressing foam formation during culture of an acetic acid bacterium by reducing or deleting the function of a protein encoded by the gene.

The present invention also provides a method wherein vinegar containing a high concentration of acetic acid is more efficiently produced by significantly suppressing foam formation during culture, and vinegar containing a high concentration of acetic acid produced by such production method is also provided.

BRIEF DESCRIPTION OF THE SEVERAL VIEWS OF THE DRAWINGS

FIG. 2 shows the aspect of foam formation when the wild-type strain and the glyT-disrupted strain were cultured in mini-jar fermenters.

FIG. 4 shows the nucleotide sequence of a DNA fragment comprising glyT (SEQ ID NO: 1).

FIG. 5 shows the amino acid sequence of a protein encoded by glyT (SEQ ID NO: 2).

FIG. 6 shows the nucleotide sequence of primer 1 (SEQ ID NO: 3).

FIG. 7 shows the nucleotide sequence of primer 2 (SEQ ID NO: 4).

FIG. 8 shows the nucleotide sequence of primer 3 (SEQ ID NO: 5).

FIG. 9 shows the nucleotide sequence of primer 4 (SEQ ID NO: 6).

DETAILED DESCRIPTION OF THE INVENTION

Figure 1:
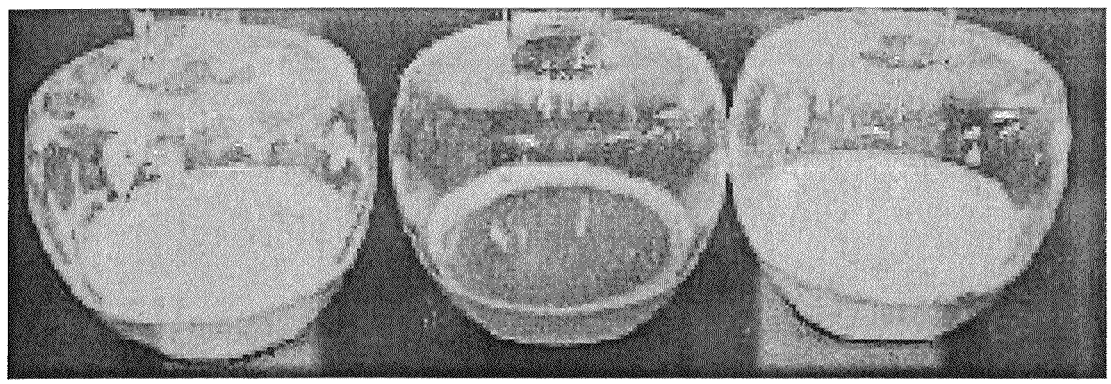
FIG. 1 shows the aspect of foam formation when the wild-type strain, the glyT-disrupted strain, and the glyT-complementary strain were cultured in Sakaguchi flasks.

The present invention relates to a gene involved in foam formation during culture of an acetic acid bacterium and a protein encoded by the gene. Further provided is an acetic acid bacterium that is capable of significantly reducing foam formation during culture and producing a larger amount of acetic acid by reducing or deleting the function of a protein encoded by the gene which is involved in foam formation during culture of an acetic acid bacterium, thereby a method is provided for suppressing foam formation during culture as well as a method for significantly enhancing the acetic acid fermentation ability using the acetic acid bacterium. The methods thus enable a more efficient production of vinegar containing a high concentration of acetic acid by using an acetic acid bacterium.

The present invention is explained in detail in the following.

The present invention relates to a protein involved in the acetic acid fermentation ability and foam formation. Specifically, it relates to a protein consisting of the amino acid sequence shown by SEQ ID NO: 2 (FIG. 5) in the sequence listing; a protein which consists of an amino acid sequence wherein one or a few amino acids are substituted, deleted, inserted or added in the amino acid sequence shown by SEQ ID NO: 2 (FIG. 5) in the sequence listing, and which is involved in foam formation during culture of an acetic acid bacterium; and a protein which consists of an amino acid sequence having at least 85% or more identity to the amino acid sequence shown by SEQ ID NO: 2 (FIG. 5) in the sequence listing, and which is involved in foam formation during culture of an acetic acid bacterium. "A protein which is involved in foam formation" in the present invention refers to a protein wherein foam formation during culture of an acetic acid bacterium is suppressed by reducing or deleting the function of the protein.

The method of obtaining and preparing a protein of the present invention is not particularly limited and the protein may be an isolated naturally-occurring protein, chemically synthesized protein, or a recombinant protein prepared by a gene recombination technique. When obtaining a naturally-occurring protein of the present invention, the protein can be identified from the cells expressing it by appropriately combining isolation and purification methods for proteins.

When preparing a protein of the present invention by chemical synthesis, the protein of the present invention can be synthesized according to a chemical synthesis method such as Fmoc method (fluorenylmethyloxycarbonyl method), tBOC method (t-butyloxycarbonyl method) or the like. A protein of the present invention can also be synthesized by utilizing various commercially-available peptide synthesizers based on the amino acid sequence information.

Further, when preparing a protein of the present invention by a gene recombination technique, a protein of the present invention can be prepared by introducing a DNA encoding the protein into a suitable expression system. Among these methods, it is preferred to prepare a protein of the present invention by a gene recombination technique which enables the preparation with a relatively easy operation at a large quantity.

When preparing a protein of the present invention by a gene recombination technique, known methods including anion- or cation-exchange chromatography; phosphocellulose chromatography; hydrophobic interaction chromatography; affinity chromatography; hydroxyapatite chromatography; and lectin chromatography may be employed after performing ammonium sulfate or ethanol precipitation and acid extraction to recover and purify the protein from the cell culture, where a high-speed liquid chromatography is preferably employed.

Particularly, the purified products of these proteins can be obtained with affinity chromatography using a column to which an antibody such as a monoclonal antibody against a protein of the present invention is bound, or a column to which a substance having affinity to the peptide tag is bound when a usual peptide tag has been added to a protein of the present invention.

Further, a protein consisting of an amino acid sequence wherein one or a few amino acids are substituted, deleted, inserted or added in the amino acid sequence shown by SEQ ID NO: 2 (FIG. 5) in the sequence listing, or a protein consisting of an amino acid sequence having at least 85% or more identity to the amino acid sequence shown by SEQ ID NO: 2 (FIG. 5) in the sequence listing can be appropriately prepared or obtained by a skilled person in the art based on the nucleotide sequence information shown by SEQ ID NO: 1 (FIG. 4) in the sequence listing, which is an example of the nucleotide sequences encoding the amino acid sequence shown by SEQ ID NO: 2 (FIG. 5).

For example, a homologue of the DNA can be isolated from acetic acid bacteria belonging to the genus *Acetobacter* or the genus *Gluconacetobacter*, or from other acetic acid bacteria by screening a homologue of the DNA under appropriate conditions by a polymerase chain reaction (PCR reaction) that uses as a primer an oligonucleotide synthesized based on the nucleotide sequence shown by SEQ ID NO: 1 (FIG. 4) in the sequence listing, or by a hybridization using as a probe an oligonucleotide synthesized based on the above nucleotide sequence. The full-length DNA of the homologous DNA is cloned, integrated into an expression vector to be expressed in an appropriate host, and the protein encoded by the homologous DNA can be prepared.

An oligonucleotide can be synthesized according to a conventional method using, for example, various commercially-available DNA synthesizers. Further, a PCR reaction can be performed according to a conventional method using a thermal cycler, Gene Amp PCR System 9700 manufactured by Applied Biosystems, with the use of TaqDNA polymerase (Takara Bio Inc.) or KOD-Plus (Toyobo Co., Ltd.).

It is also possible to bind the protein of the present invention with a marker protein and/or a peptide tag to provide a fusion protein. The marker protein is not particularly limited as long as it is a conventionally known marker protein. Specific examples of the marker protein include enzymes such as alkaline phosphatase and HRP, the Fc region of an antibody, and a fluorescent material such as GFP. Further, specific examples of the peptide tag include conventionally known peptide tags including epitope tags such as HA, FLAG, Myc; and affinity tags such as GST, maltose-binding protein, biotinated peptide, and oligohistidine. The fusion protein can be produced by a common method, and is useful for purification of a protein of the present invention, detection of a protein of the present invention and quantitative determination of an antibody against a protein of the present invention by utilizing affinity between Ni-NTA and His tag. The fusion protein is also useful as a laboratory reagent in the field to which the present invention pertains.

A protein of the present invention can be confirmed to be a protein involved in foam formation during culture of an acetic acid bacterium by, for example, producing an acetic acid bacterium in which the function of the protein is reduced or deleted, culturing the acetic acid bacterium in a liquid medium containing alcohol under an aerobic condition, and then comparing the degree of foam formation during culture to that of the wild-type strain. An acetic acid bacterium in which the function of a protein of the present invention is reduced or deleted can be produced by transforming an acetic acid bacterium with a DNA comprising a modified gene which has been modified so as not to produce a normally functioning protein by, for example, deleting a partial sequence of a gene encoding the protein or by inserting a drug-resistant gene into the gene, then by disrupting a normal gene on the chromosome with the modified gene by a homologous recombination.

Further, examples of a DNA of the present invention include: a DNA encoding a protein consisting of the amino acid sequence shown by SEQ ID NO: 2 (FIG. 5) in the sequence listing; a DNA encoding a protein which consists of an amino acid sequence wherein one or a few amino acids are substituted, deleted, inserted or added in the amino acid sequence shown by SEQ ID NO: 2 (FIG. 5) in the sequence listing, and which is involved in foam formation during culture of an acetic acid bacterium; a DNA encoding a protein which consists of an amino acid sequence having at least 85% or more identity to the amino acid sequence shown by SEQ ID NO: 2 (FIG. 5) in the sequence listing, and which is involved in foam formation during culture of an acetic acid bacterium; a DNA consisting of the nucleotide sequence of nucleotide numbers 846 to 3794 in the nucleotide sequence shown by SEQ ID NO: 1 (FIG. 4) in the sequence listing; a DNA which hybridizes under stringent conditions to a DNA consisting of a sequence complementary to the nucleotide sequence of nucleotide numbers 846 to 3794 in the nucleotide sequence shown by SEQ ID NO: 1 (FIG. 4) in the sequence listing, and which encodes a protein involved in foam formation during culture of an acetic acid bacterium; a DNA which hybridizes under stringent conditions to a DNA consisting of a nucleotide sequence produced from a part of the nucleotide sequence of nucleotide numbers 846 to 3794 in the nucleotide sequence shown by SEQ ID NO: 1 (FIG. 4) in the sequence listing and having the function as a primer or a probe, and which encodes a protein involved in foam formation during culture of an acetic acid bacterium; and a DNA which consists of a nucleotide sequence wherein one or a few nucleotides are substituted, deleted, inserted or added in the nucleotide sequence of nucleotide numbers 846 to 3794 in the nucleotide sequence shown by SEQ ID NO: 1 (FIG. 4) in the sequence listing, and which encodes a protein involved in foam formation during culture of an acetic acid bacterium.

As stated above, a DNA encoding a protein involved in foam formation during culture of an acetic acid bacterium of the present invention may be a DNA that encodes a protein having deletion, substitution, insertion or addition of one or a few amino acids at a single site or plural sites, as long as the function of the encoded protein is not impaired.

A DNA encoding a protein that is substantially the same as a protein having the function of a protein involved in foam formation during culture of an acetic acid bacterium can be obtained by alteration of a nucleotide sequence, such modification being a deletion, substitution, insertion, addition, or inversion of an amino acid at a particular site by means of, for example, site-directed mutagenesis. Further, an altered DNA such as the above can also be obtained by a conventionally known mutagenic treatment. Still further, it is possible to obtain a DNA that encodes substantially the same protein from acetic acid bacteria in general, or particularly from species, strains, mutants or variants of the genus *Acetobacter* or the genus *Gluconacetobacter*, because it is generally known that an amino acid sequence of a protein and a nucleotide sequence encoding the same are slightly different among the species, strains, mutants or variants.

The above "amino acid sequence wherein one or a few amino acids are substituted, deleted, inserted or added" means, for example, an amino acid sequence wherein any number of amino acids, for example, 1 to 20, preferably 1 to 15, more preferably 1 to 10, and still more preferably 1 to 5 amino acids, are substituted, deleted, inserted or added.

Further, the above "nucleotide sequence wherein one or a few nucleotides are substituted, deleted, inserted or added" means, for example, a nucleotide sequence wherein any number of nucleotides, for example, 1 to 20, preferably 1 to 15, more preferably 1 to 10, and still more preferably 1 to 5 nucleotides are substituted, deleted, inserted or added.

For example, these DNAs consisting of a nucleotide sequence comprising a substitution, deletion, insertion, or addition of one or a few nucleotides (mutated DNAs) can also be prepared by any method known to a skilled person in the art, such as chemical synthesis, genetic engineering technique, and mutagenesis, as stated above. Specifically, mutated DNAs can be obtained by introducing a mutation into the DNA consisting of the nucleotide sequence shown by SEQ ID NO: 1 (FIG. 4) in the sequence listing, using a method of allowing a mutagenic agent to contact with and act on the DNA; a method of irradiating the DNA with ultraviolet; a genetic engineering technique or the like.

The site-directed mutagenesis, one of the genetic engineering techniques, is useful as it is a technique that allows an introduction of a specific mutation into a specific site, and can be performed according to the method described in Molecular Cloning: A laboratory Manual, 2nd Ed., Cold Spring Harbor Laboratory, Cold Spring Harbor, N.Y., 1989, or in Current Protocols in Molecular Biology, Supplement 1-38, John Wiley & Sons (1987-1997). An expression of this mutated DNA using an appropriate expression system provides a protein consisting of an amino acid sequence comprising a substitution, deletion, insertion or addition of one or a few amino acids.

The above "amino acid sequence having at least 85% or more identity to the amino acid sequence shown by SEQ ID NO: 2 (FIG. 5) in the sequence listing" is not particularly limited as long as the identity to the amino acid sequence shown by SEQ ID NO: 2 (FIG. 5) in the sequence listing is 85% or more. This means that the identity is, for example, 85% or more, preferably 90% or more, more preferably 95% or more, and particularly preferably 98% or more.

The above "under stringent conditions" refers to a condition under which a so-called specific hybrid is formed while a non-specific hybrid is not formed. Specific examples include a condition under which DNAs sharing 50% or more, preferably 70% or more identity hybridize each other, while DNAs with the lower identity do not hybridize; or a hybridization condition at a salt concentration corresponding to 1×SSC (1-fold-concentration SSC solution comprises 150 mM NaCl and 15 mM sodium citrate) and 0.1% SDS, or 0.1×SSC and 0.1% SDS at 65° C., which are washing conditions for a usual southern hybridization.

Further, the above "DNA that hybridizes under stringent conditions" means a DNA that can be obtained by using a method such as a colony hybridization, plaque hybridization or southern-blot hybridization using nucleic acids such as DNA or RNA as a probe. Specifically exemplified is a DNA that can be identified by conducting a hybridization at 65° C. in the presence of 0.7 to 1.0 M NaCl using a filter on which a colony- or plaque-derived DNA or a fragment thereof is immobilized, and washing the filter under the condition of 65° C. with about 0.1 to 2-fold-concentration SSC solution.

Hybridization can be performed according to the method described in Molecular Cloning, 2nd Ed. Examples of the DNA that can hybridize under stringent conditions include a DNA having an identity above a certain level to a nucleotide sequence of a DNA used as a probe. A DNA having an identity of, for example, 60% or more, preferably 70% or more, more preferably 80% or more, still more preferably 90% or more, particularly preferably 95% or more, and most preferably 98% or more, can be exemplified advantageously.

The method of obtaining or preparing a DNA of the present invention is not particularly limited. The DNA of interest can be isolated by preparing an appropriate probe or primer based on the nucleotide sequence information shown by SEQ ID NO: 1 (FIG. 4) in the sequence listing or the amino acid sequence information shown by SEQ ID NO: 2 (FIG. 5) in the sequence listing disclosed herein, and using the probe or primer for screening a cDNA library where the DNA is expected to be present, or the DNA can be prepared by chemical synthesis according to a common method.

A DNA of the present invention can be obtained, for example, by preparing a cDNA library according to a common method from acetic acid bacteria belonging to the genus *Acetobacter* or the genus *Gluconacetobacter*, and then selecting from this library the desired clone by using an appropriate probe specific to a DNA of the present invention. Further, isolation of total RNA, isolation and purification of mRNAs, acquisition and cloning of cDNAs and the like from these acetic acid bacteria can all be performed according to a common method. Examples of the method of screening a DNA of the present invention from a cDNA library include the methods commonly used by a skilled person in the art such as the method described in Molecular Cloning, 2nd ed.

Since the nucleotide sequence of the DNA of the present invention has already been elucidated, the DNA can be obtained by a PCR reaction using the oligonucleotide synthesized based on the nucleotide sequence as a primer or by hybridization using the oligonucleotide synthesized based on the nucleotide sequence as a probe, with the use of, for example, the genomic DNA of the acetic acid bacterium, *Gluconacetobacter intermedius* NCI1051 (FERM BP-10767), as a template. The chromosomal DNA can be obtained by a common method (e.g., a method disclosed in Japanese Laid-Open Patent Application No. 60-9489).

An oligonucleotide can be synthesized according to a common method using, for example, various commercially-available DNA synthesizers. Further, a PCR reaction can be performed according to a common method using a thermal cycler, Gene Amp PCR System 9700 manufactured by Applied Biosystems, with the use of TaqDNA polymerase (Takara Bio Inc.), KOD-Plus (Toyobo Co., Ltd.), etc.

A DNA of the present invention can be obtained by alteration of a nucleotide sequence, such alteration being a deletion, substitution, insertion or addition of amino acids at a specific site by means of, for example, site-directed mutagenesis. Further, an altered DNA such as the above can also be obtained by a conventionally known mutagenic treatment.

Still further, it is possible to obtain a DNA that encodes substantially the same protein from general acetic acid bacteria, particularly from species, strains, mutants or variants of the genus *Acetobacter* or the genus *Gluconacetobacter*, because it is generally known that an amino acid sequence of a protein and a nucleotide sequence encoding the same are slightly different among the species, strains, mutants or variants.

It is also possible to obtain a DNA encoding a protein that is substantially the same as the above protein, specifically by isolating a DNA which hybridizes under stringent conditions to a DNA comprising a nucleotide sequence described in the nucleotide sequence shown by SEQ ID NO: 1 (FIG. 4) in the sequence listing and which encodes a protein involved in foam formation during culture of an acetic acid bacterium from acetic acid bacteria belonging to the genus *Acetobacter* or the genus *Gluconacetobacter*, or mutated acetic acid bacteria belonging to the genus *Acetobacter* or the genus *Gluconacetobacter*, or from spontaneous mutants or variants thereof.

A mutant gene or homologous gene of the present invention consisting of a DNA encoding a protein consisting of an amino acid sequence wherein one or a few amino acids are substituted, deleted, inserted or added in the amino acid sequence shown by SEQ ID NO: 2 (FIG. 5) in the sequence listing and involved in foam formation during culture of an acetic acid bacterium, or a DNA encoding a protein consisting of an amino acid sequence having at least 85% or more identity to the amino acid sequence shown by SEQ ID NO: 2 (FIG. 5) in the sequence listing and having a function as a protein involved in foam formation during culture of an acetic acid bacterium, can be isolated from other acetic acid bacteria or the like by screening a homologue of the above DNA under appropriate conditions with the use of a DNA fragment comprising the nucleotide sequence shown by SEQ ID NO: 1 (FIG. 4) in the sequence listing or a part thereof. The variant gene or homologous gene can also be prepared by a production method of an altered DNA as described above.

It is also possible to obtain a DNA encoding a protein that is substantially the same as the above protein by isolating a DNA which hybridizes under stringent conditions to a probe prepared from the nucleotide sequence shown by SEQ ID NO: 1 (FIG. 4) in the sequence listing or from a part thereof from acetic acid bacteria belonging to the genus *Acetobacter* or the genus *Gluconacetobacter*, or mutated acetic acid bacteria belonging to the genus *Acetobacter* or the genus *Gluconacetobacter*, or from spontaneous mutants or variants thereof, and which encodes a protein involved in foam formation during culture of an acetic acid bacterium.

An acetic acid bacterium for use in the present invention is not particularly limited and is exemplified by a bacterium belonging to such genus as *Acetobacter* or *Gluconacetobacter* and having alcohol oxidation ability, as exemplified below.

Examples of the acetic acid bacterium belonging to the genus *Gluconacetobacter* include *Gluconacetobacter intermedius, Gluconacetobacter xylinus, Gluconacetobacter europaeus, Gluconacetobacter diazotrophicus* and *Gluconacetobacter entanii*, and more specifically include *Gluconacetobacter xylinus* IFO3288, *Gluconacetobacter europaeus* DSM6160, *Gluconacetobacter diazotrophicus* ATCC49037, *Acetobacter altoacetigenes* MH-24, and *Gluconacetobacter intermedius* NCI1051 (FERM BP-10767).

Further, examples of the acetic acid bacterium belonging to the genus *Acetobacter* include *Acetobacter aceti*, and more specifically include *Acetobacter aceti* No. 1023 and *Acetobacter aceti* IFO3283.

A DNA of the present invention can be confirmed to be a DNA encoding a protein involved in foam formation during culture of an acetic acid bacterium by, for example, producing an acetic acid bacterium in which the DNA is deficient, culturing the acetic acid bacterium in a liquid medium containing alcohol under an aerobic condition, and then comparing the degree of foam formation during culture to that of the wild-type strain. An acetic acid bacterium in which the DNA of the present invention is deficient can be produced by transforming an acetic acid bacterium with a DNA comprising a modified gene prepared by, for example, deleting a partial sequence of the DNA or by inserting a drug-resistant gene into the DNA sequence, and disrupting a normal gene on the chromosome with the modified gene by homologous recombination.

The method of the present invention for suppressing foam formation during culture of an acetic acid bacterium by reducing or deleting the function of a protein encoded by the gene involved in foam formation during culture of an acetic acid bacterium (i.e., a gene encoding a protein involved in foam formation during culture of an acetic acid bacterium) includes a method which comprises culturing an acetic acid bacterium under the physical conditions that inhibit the expression of the gene encoding the foam-forming protein or the activity of the protein encoded by the gene.

It is also effective to reduce or delete the function by modifying a gene involved in foam formation during culture of an acetic acid bacterium. It is also effective to induce mutation in a region of the gene involved in the expression of the gene so as to inhibit the expression thereof. As a method to modify a gene, a method in which mutation is induced to the gene by a physical treatment or by using a chemical mutagenic agent is effective. These conventionally practiced methods for inducing mutation are effective for acetic acid bacteria. Examples of such conventional method include a method for inducing mutation by subjecting an acetic acid bacterium to an ultraviolet irradiation or treating an acetic acid bacterium with N-methyl-N'-nitro-N-nitrosoguanidine (NTG) or with a mutagenic agent usually used for mutagenic treatment such as nitrous acid.

Since acetic acid bacteria are known as bacteria that tend to mutate spontaneously, an acetic acid bacterium with suppressed foam formation during culture of an acetic acid bacterium can also be obtained by isolating from nature an acetic acid bacterium having a gene in which expression or function of the above enzyme has been spontaneously mutated. Further, since these genes have already been obtained and the nucleotide sequences thereof have also been elucidated, it is also effective to subject these genes to recombination for introducing mutagenesis, then to introduce the mutated gene into the original acetic acid bacterium, and to reduce or delete the function of the gene of the original acetic acid bacterium by employing a technique such as a homologous recombination.

A method to reduce or delete the function of the gene of the present invention is effective wherein the method comprises: transforming an acetic acid bacterium with a DNA comprising a modified gene that has been modified so as not to produce a normally functioning protein involved in foam formation during culture of an acetic acid bacterium by, for example, deleting a partial sequence of the gene or by inserting a drug-resistant gene into the gene; and then disrupting a normal gene on the chromosome with the modified gene by a homologous recombination.

Further, when a gene involved in foam formation during culture of an acetic acid bacterium of the present invention is controlled by the quorum-sensing system, it is also possible to reduce or delete the function of a protein encoded by the gene involved in foam formation during culture of an acetic acid bacterium by reducing or deleting the function of the quorum-sensing system. For example, an acetic acid bacterium with suppressed foam formation during culture of an acetic acid bacterium wherein the function of the Acyl Homoserine Lactone Synthase and/or the Acyl Homoserine Lactone Receptor-Type Transcription Factor is reduced or deleted can be prepared by disrupting the gene of Acyl Homoserine Lactone Synthase (orf1) and/or the gene of Acyl Homoserine Lactone Receptor-Type Transcription Factor (orf2).

Transformation of an acetic acid bacterium may be conducted by a calcium chloride method (see for example, Agric. Biol. Chem., Vol. 49, p. 2091, 1985), and an electroporation method (see for example, Proc. Natl. Acad. Sci. U.S.A., Vol. 87, pp. 8130-8134, 1990).

As stated above, foam formation during culture of an acetic acid bacterium can be suppressed in an acetic acid bacterium belonging to the genus *Acetobacter* or the genus *Gluconacetobacter* having the alcohol oxidation ability by altering a protein involved in foam formation during culture of an acetic acid bacterium by reducing or deleting the function as described above so that the protein does not function normally.

The acetic acid bacterium with suppressed foam formation during culture of an acetic acid bacterium of the present invention is exemplified by *Gluconacetobacter intermedius* NCI1051ΔglyT (FERM BP-11068).

A conventionally known method is employed for the method of producing vinegar of the present invention except that the function of a protein involved in foam formation during culture of an acetic acid bacterium is reduced or deleted so that the protein does not function normally, and culturing the acetic acid bacterium in an alcohol-containing medium to generate and accumulate acetic acid in the medium. Namely, an acetic acid bacterium may be cultured basically under the conditions where acetic acid fermentation can be performed. Specifically, the culture of an acetic acid bacterium may be conducted similarly to a vinegar producing culture that employs a conventional method for acetic acid fermentation.

As for an alcohol-containing medium, any medium suffices as long as it is a medium used for acetic acid fermentation. Any alcohol-containing media may be used that contains a carbon source, nitrogen source, inorganic substance, etc., other than an alcoholic component such as ethanol, as long as it contains an appropriate amount of nutrient source required for growth of the bacterial strain in use. A medium may be either a synthetic medium or a natural medium. Examples of the carbon source include various carbohydrates including glucose and sucrose, and various organic acids. As for the nitrogen source, a natural nitrogen source such as peptone, degradation product of microbial cells or the like can be used.

Further, the culture is performed under an aerobic condition such as in a static culture, shaking culture, aeration-agitation culture and the like. The culture temperature is usually in the range of 25 to 35° C., preferably at 30° C. The pH of the medium is generally within the range of 2.5 to 7, preferably within the range of 2.7 to 6.5, and the pH can also be adjusted with various acids, various bases, buffers or the like. Generally, a 1- to 21-day culture can accumulate a high concentration of acetic acid in the medium. Thus, a high acidity vinegar with suppressed foam formation during culture of an acetic acid bacterium can be produced more efficiently by the above method for producing vinegar of the present invention.

The present invention is specifically explained in the following examples. The technical scope of the present invention, however, will not be limited to these exemplifications.

Example 1

Searching a Gene which is Under the Control of the Quorum-Sensing System

The present inventor had demonstrated that the quorum-sensing system controls foam formation during the culture of an acetic acid bacterium, but it had been unknown as to what gene is controlled by the quorum-sensing system and what gene is involved in foam formation during culture of an acetic acid bacterium. Therefore, a microarray analysis was conducted to identify a gene which is under the control of the quorum-sensing system and to search for a gene involved in foam formation during culture of an acetic acid bacterium.

Specifically, RNA was extracted from *Gluconacetobacter intermedius* NCI1051 (hereinafter may be referred to as wild-type strain) and *Gluconacetobacter intermedius* NCI1051Δorf1 (hereinafter may be referred to as orf1-disrupted strain), and the expression levels thereof were compared by microarray analysis employing a unicolor method (see for example, "Lab Manual, DNA chip and realtime PCR, Kodansha Limited, 2005"). Here, *Gluconacetobacter intermedius* NCI1051 is deposited under the Budapest Treaty with the International Patent Organism Depositary at the National Institute of Advanced Industrial Science and Technology (Central 6, 1-1 Higashi 1-Chome, Tsukuba-shi, Ibaraki-ken, Japan) under the Accession Number FERM BP-10767, and *Gluconacetobacter intermedius* NCI1051Δorf1, in which a gene encoding the acyl homoserine lactone synthase (orf1) is disrupted, that is one of the components of the quorum-sensing system, is deposited under the Budapest Treaty with the same depositary under the Accession Number FERM BP-10768.

First, the wild-type strain and the orf1-disrupted strain were cultured at 30° C. and 120 spm by a shaking culture in a medium (100 ml) containing 2% ethanol, 3% glucose, 0.5% yeast extract, 0.3% polypeptone, and 1% Celluclast 1.5 L (Novozymes) using a Sakaguchi flask of 500 ml volume. RNA was extracted using RNeasy (QIAGEN) from the culture broth of both strains at the logarithmic phase and the early stationary phase. Quality of the RNA was confirmed by Bioanalyzer (Agilent).

Each RNA extracted was used as a template to synthesize cDNA using a reverse transcriptase and random primers, and the terminal end of the cDNA was labeled with biotin. Separately, a microarray arranged with specific probes corresponding to all the genes on the genome was designed and generated. Subsequently, the biotin-labeled cDNA synthesized beforehand was hybridized to the microarray according to a common method and the expression levels of all the genes were quantified. Hybridization was conducted for a sample derived from the wild-type strain and a sample derived from the orf1-disrupted strain. The expression data was normalized using Robust Multi-chip Analysis (RMA) and employed as the expression intensity of each gene.

As a result of comparison of the expression intensity obtained by the above-mentioned microarray analysis for each gene of the wild-type strain and the orf1-disrupted strain, a gene was found in which the transcript amount was significantly decreased in the orf1-disrupted strain as compared to the wild-type strain. This gene (hereinafter may be referred to as glyT) had the nucleotide sequence of nucleotide numbers 846 to 3794 in SEQ ID NO: 1 (FIG. 4) in the sequence listing, and the protein encoded by the gene had the amino acid sequence shown by SEQ ID NO: 2 (FIG. 5) in the sequence listing.

As a result of the homology search by BLAST (http://blast.ncbi.nlm.nih.gov/Blast.cgi), the protein encoded by glyT showed 44% identity at the amino acid level to each of the proteins presumed to be glycosyltransferase in *Gluconacetobacter diazotrophicus* PAL5 and *Gluconobacter oxydans* 621H. However, function of these proteins was not previously analyzed, and before this invention it was totally unknown that the proteins are involved in foam formation during culture or that the proteins are involved in the acetic acid fermentation ability of acetic acid bacteria.

Further, transcript analysis was conducted for glyT by S1 nuclease mapping method (see for example, Journal of Bacteriology, Vol. 180, pp. 2515-2521, 1988) in order to confirm the results of the microarray analysis. The result confirmed that the transcript amount of glyT was significantly decreased in the orf1-disrupted strain as compared to the wild-type strain, and it was thus confirmed that glyT is a gene which is under the control of the quorum-sensing system.

Example 2

Obtaining the glyT-Disrupted Strain

To investigate whether or not glyT, found in Example 1 was under the control of the quorum-sensing system and was involved in foam formation during culture of an acetic acid bacterium, a glyT-disrupted strain was prepared from *Gluconacetobacter intermedius* NCI1051 by the following procedures.

First, a DNA fragment of 2.3 kb including a part of glyT (nucleotide numbers 1 to 2252 in SEQ ID NO: 1 in the sequence listing (FIG. 4)) was obtained by colony hybridization and the DNA fragment was inserted into the PstI site of pUC19 to prepare a plasmid (hereinafter may be referred to as plasmid 1). Next, a DNA fragment including a kanamycin-resistant gene was amplified by PCR method using primer 1 (see SEQ ID NO: 3 in the sequence listing (FIG. 6)) and primer 2 (see SEQ ID NO: 4 in the sequence listing (FIG. 7)) with transposon Tn5 of *Escherichia coli* as a template. The amplified product was then treated with the restriction enzyme Sma I (TAKARA BIO INC.) to prepare a DNA fragment (hereinafter may be referred to as DNA fragment 1).

The DNA fragment 1 was ligated by a ligation reaction to the plasmid 1 which was digested with the restriction enzyme EcoRV (TAKARA BIO INC.). *Escherichia coli* JM109 strain was transformed with the DNA thus prepared. Transformants were selected on an LB agar medium supplemented with 100

µg/ml ampicillin. The plasmid pUCΔglyT for disrupting glyT was recovered from the selected ampicillin-resistant transformant according to a common method.

The plasmid pUCΔglyT for disrupting glyT obtained as stated above was used to transform *Gluconacetobacter intermedius* NCI1051 by electroporation method (see for example, Proc. Natl. Acad. Sci. U.S.A., Vol. 87, pp. 8130-8134, 1990).

Transformants were selected on a YPG medium (3% glucose, 0.5% yeast extract, 0.3% polypeptone) supplemented with 100 µg/ml kanamycin. The kanamycin-resistant transformant grown on the selection medium was confirmed by southern hybridization to be a strain in which glyT has been disrupted by insertion of the kanamycin-resistant gene into glyT.

One of the strains among the obtained transformants was named as *Gluconacetobacter intermedius* NCI1051ΔglyT (hereinafter may be referred to as glyT-disrupted strain) and deposited under the Budapest Treaty with the International Patent Organism Depositary at the National Institute of Advanced Industrial Science and Technology (Central 6, 1-1 Higashi 1-Chome, Tsukuba-shi, Ibaraki-ken, Japan). The Accession Number is FERM BP-11068 and the date of depositary is Dec. 2, 2008.

In order to confirm that the phenotype of the glyT-disrupted strain is attributed to the disruption of glyT gene, a complementary plasmid pGlyT comprising glyT gene was introduced into the glyT-disrupted strain to produce a glyT complementary strain.

First, the plasmid pGlyT comprising glyT gene was produced as follows. Specifically, plasmid 1 mentioned above was digested with the restriction enzymes EcoRI and ApaI (TAKARA BIO INC.) to prepare a DNA fragment including the 5' side region of glyT (hereinafter may be referred to as DNA fragment 2).

Next, a DNA fragment including the 3' side region of glyT was amplified by PCR method using primer 3 (see SEQ ID NO: 5 in the sequence listing (FIG. 8)) and primer 4 (see SEQ ID NO: 6 in the sequence listing (FIG. 9)) with the genomic DNA of *Gluconacetobacter intermedius* NCI1051 as a template. The amplified product was then treated with the restriction enzymes ApaI and XbaI (TAKARA BIO INC.) to prepare a DNA fragment (hereinafter may be referred to as DNA fragment 3).

The DNA fragments 2 and 3 were ligated by a ligation reaction to the shuttle vector pMV24 between *Escherichia coli* and acetic acid bacteria which was digested with the restriction enzymes EcoRI and XbaI (TAKARA BIO INC.). The DNA thus prepared was used to transform *Escherichia coli* JM109 strain. Transformants were selected on a LB agar medium supplemented with 100 µg/ml ampicillin. The complementary plasmid pGlyT was recovered from the selected ampicillin-resistant transformant according to a common method.

The complementary plasmid pGlyT thus obtained was used to transform *Gluconacetobacter intermedius* NCI1051ΔglyT by electroporation method.

Transformants were selected on a YPG medium (3% glucose, 0.5% yeast extract, 0.3% polypeptone) supplemented with 100 µg/ml ampicillin. A plasmid was extracted from the ampicillin-resistant transformant grown on the selection medium and it was confirmed that pGlyT had been introduced. The obtained transformant was used as a glyT complementary strain.

Example 3

Comparing Foam Formation Between the glyT-Disrupted Strain and the Wild-Type Strain The glyT-disrupted strain obtained in Example 2 was compared to the wild-type strain and the glyT complementary strain for the aspect of foam formation during culture. Specifically, a shaking culture was carried out at 30° C. and 120 spm in a medium (100 ml) containing 2% ethanol, 3% glucose, 0.5% yeast extract, 0.3% polypeptone, and 1% Celluclast 1.5 L (Novozymes) by using a 500-ml Sakaguchi flask.

The result demonstrated that foam formation was significantly suppressed in the glyT-disrupted strain as compared to the wild-type strain (FIG. 1). Further, since foam formation in the glyT complementary strain was restored to the level of the wild-type strain (FIG. 1), it was confirmed that the suppression of foam formation observed in the glyT-disrupted strain was due to the disruption of glyT.

Next, the aspect of foam formation during culture was further compared in a mini-jar fermenter between the glyT-disrupted strain and the wild-type strain. An aeration-agitation culture was carried out at 30° C., 500 rpm and 1 L/min in a medium (1.5 L) containing 3% ethanol, 3% glucose, 0.5% yeast extract, 0.3% polypeptone, 100 µg/ml ampicillin, 1% Celluclast 1.5 L (Novozymes) and 0.01% antifoaming agent by using a 3-liter mini-jar fermenter (Bioneer 300, 3 L; B.E. MARUBISHI Co. Ltd.). The ethanol concentration in the medium was controlled at 2% during culture.

The aspect of foam formation in the mini-jar fermenter was shown in FIG. 2. As demonstrated from FIG. 2, foam formation was significantly suppressed in the glyT-disrupted strain as compared to the wild-type strain. This result shows that glyT is involved in foam formation during culture and that foam formation during culture is significantly suppressed by disrupting glyT.

Example 4

Comparing the Acetic Acid Fermentation Ability of the glyT-Disrupted Strain and the Wild-Type Strain The glyT-disrupted strain obtained in Example 2 was compared to the wild-type strain for acetic acid fermentation ability. Specifically, an aeration-agitation culture was carried out at 30° C., 500 rpm and 1 L/min in a medium (1.5 L) containing 3% ethanol, 3% glucose, 0.5% yeast extract, 0.3% polypeptone, 1% Celluclast 1.5 L (Novozymes) and 0.01% antifoaming agent by using a 3-liter mini-jar fermenter (Bioneer 300, 3 L; B.E. MARUBISHI Co. Ltd.). The ethanol concentration in the medium was controlled at 2% during culture. Time course of the acetic acid fermentation is shown in FIG. 3 and the acetic acid concentration of the culture broth after 48 hours of culture is shown in Table 1.

TABLE 1

|  | Wild-type strain | glyT-disrupted strain |
|---|---|---|
| Acetic acid concentration (% wt/vol) | 2.67 ± 0.07 | 5.32 ± 0.23 |

Figure 3:
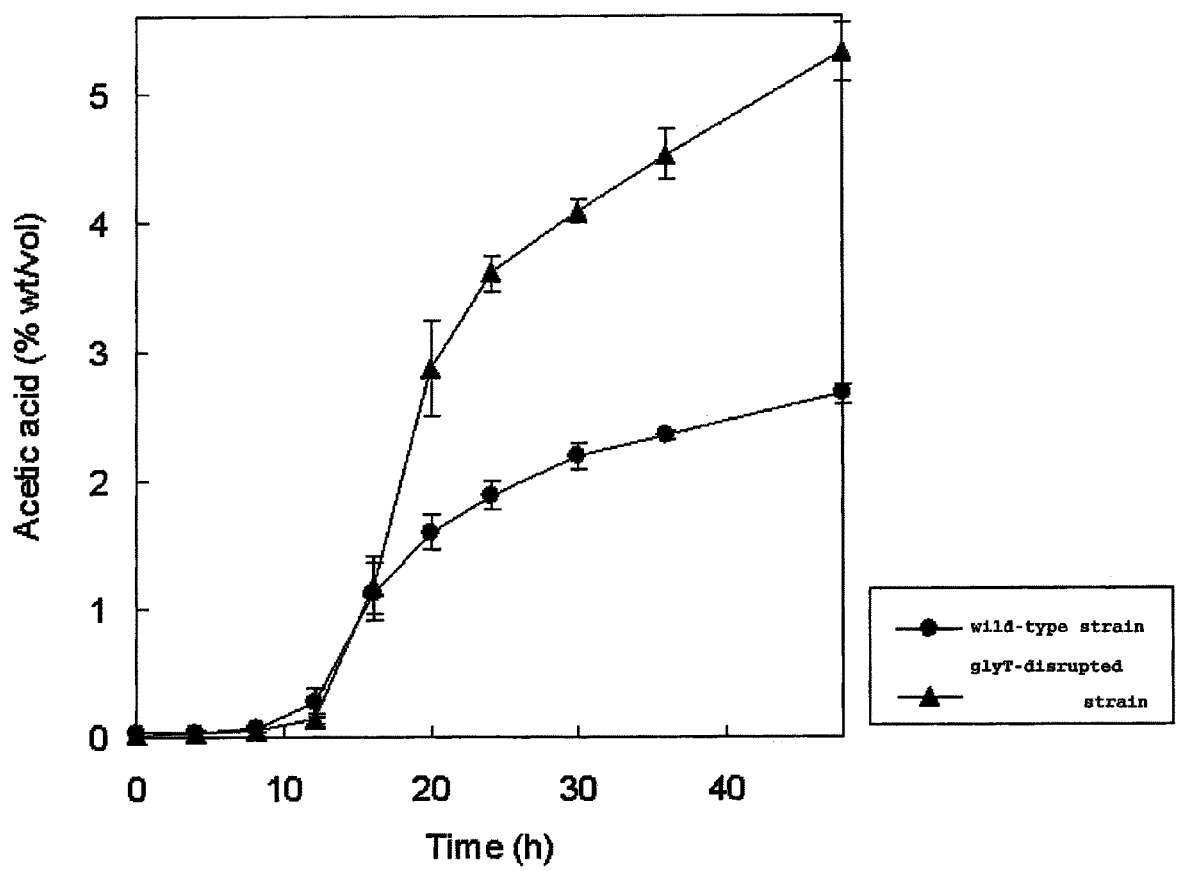
FIG. 3 shows the time course of acetic acid fermentation of the wild-type strain and the glyT-disrupted strain.

As is clear from FIG. 3, the yield of acetic acid was significantly increased in the glyT-disrupted strain as compared to the wild-type strain. Also, as shown in Table 1, an acetic acid concentration of the culture solution after 48 hours of culture was 5.32±0.23% (weight/volume) for the glyT-disrupted strain as compared to 2.67±0.07% (weight/volume) for the wild-type strain, showing that the acetic acid production amount of the glyT-disrupted strain was increased by about 2-fold against that of the wild-type strain. The above results demonstrated that glyT is also involved in acetic acid production and that disruption of glyT not only leads to a significant suppression of foam formation during culture but also leads to a more efficient production of vinegar containing a higher concentration of acetic acid.

The invention claimed is:

1. A method for producing an acetic acid bacterium with suppressed foaming ability, said method comprising modifying a gene encoding an endogenous protein involved in foam formation in the acetic acid bacterium to reduce the activity of said endogenous protein to mediate foam formation, wherein
   (I) said endogenous protein involved in foam formation is selected from the group consisting of:
      (A) the protein encoded by the nucleotide sequence set forth by nucleotides 846 to 3794 of SEQ ID NO: 1;
      (B) a protein encoded by a nucleotide sequence that is at least 95% identical to nucleotides 846 to 3794 of SEQ ID NO: 1;
      (C) a protein encoded by a nucleotide sequence wherein 1 to 20 nucleotides are substituted, deleted, inserted or added in the nucleotide sequence of nucleotides 846 to 3794 of SEQ ID NO:1;
      (D) the protein of SEQ ID NO: 2;
      (E) a protein consisting of an amino acid sequence wherein 1 to 20 amino acids are substituted, deleted, inserted or added in the amino acid sequence shown by SEQ ID NO: 2; and
      (F) a protein consisting of an amino acid sequence that is at least 95% identical to SEQ ID NO:2, and
   (II) the acetic acid bacterium is a bacterium selected from the group consisting of the genus *Acetobacter*, the genus *Gluconobacter*, and the genus *Gluconacetobacter*, and has an acetic acid generating ability by alcohol oxidation.

* * * * *